United States Patent
Eastman et al.

(10) Patent No.: US 11,298,201 B2
(45) Date of Patent: Apr. 12, 2022

(54) STERILE DRAPE FOR A SURGICAL DISPLAY AND METHOD RELATED THERETO

(71) Applicant: Johnson & Johnson Surgical Vision, Inc., Irvine, CA (US)

(72) Inventors: Brian Eastman, Irvine, CA (US); James Gerg, Lake Forest, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 49 days.

(21) Appl. No.: 14/193,510

(22) Filed: Feb. 28, 2014

(65) Prior Publication Data
US 2014/0261455 A1    Sep. 18, 2014

Related U.S. Application Data

(60) Provisional application No. 61/791,603, filed on Mar. 15, 2013.

(51) Int. Cl.
*A61B 46/10* (2016.01)
*A61B 17/00* (2006.01)

(52) U.S. Cl.
CPC .... *A61B 46/10* (2016.02); *A61B 2017/00902* (2013.01)

(58) Field of Classification Search
CPC ..... A61B 19/081; A61B 19/088; A61B 19/08; A61B 46/00–40; A61B 50/00; A61B 2050/001–009; A61B 2017/00902; A61B 17/00; G06F 1/16–1603
See application file for complete search history.

(56) References Cited

U.S. PATENT DOCUMENTS

| | | | | |
|---|---|---|---|---|
| 3,037,507 A * | 6/1962 | Melges | A61B 46/00 128/856 |
| 3,335,719 A * | 8/1967 | Boucher | A61B 46/00 128/855 |
| 3,540,441 A * | 11/1970 | Collins | A61B 46/00 128/855 |
| 3,589,365 A * | 6/1971 | Sejman | A61B 46/30 604/357 |
| 3,707,964 A | 1/1973 | Patience et al. | |
| 5,379,703 A * | 1/1995 | Marshall | A61B 46/10 108/90 |
| 5,970,980 A | 10/1999 | Adair | |

(Continued)

FOREIGN PATENT DOCUMENTS

WO     WO-0197866 A2     12/2001

OTHER PUBLICATIONS

International Search Report and Written Opinion for Application No. PCT/US2014/019399, dated Apr. 15, 2014, 11 pages.

*Primary Examiner* — Michelle J Lee
(74) *Attorney, Agent, or Firm* — Johnson & Johnson Surgical Vision, Inc.

(57) ABSTRACT

A method of providing a sterile drape for covering a display of a phacoemulsification console may include providing the sterile drape in a sterile package dedicated for a patient, enabling removal of the sterile drape from the package by a sterile user, providing a finger guard pocket in the sterile drape suitable for receiving fingers of the sterile user, and providing a fitted pocket to allow for fitting of the sterile drape over the display.

15 Claims, 7 Drawing Sheets

(56) References Cited

U.S. PATENT DOCUMENTS

| | | | |
|---|---|---|---|
| 2001/0023697 A1* | 9/2001 | Hinley, Jr. | A61B 46/40 128/852 |
| 2003/0075183 A1* | 4/2003 | Faries, Jr. | A61B 19/081 128/849 |
| 2004/0118409 A1* | 6/2004 | Griesbach, III | A61B 46/00 128/849 |
| 2006/0052025 A1* | 3/2006 | Dharmadhikary | B32B 7/02 442/398 |
| 2006/0235436 A1 | 10/2006 | Anderson et al. | |
| 2008/0112842 A1* | 5/2008 | Edwards | G06F 1/1601 422/2 |
| 2011/0174318 A1* | 7/2011 | Reyes | A61B 46/23 128/852 |
| 2011/0197897 A1* | 8/2011 | Touati | A61B 17/02 128/853 |

* cited by examiner

STERILE DRAPE FOR A SURGICAL DISPLAY AND METHOD RELATED THERETO

CROSS-REFERENCE TO RELATED CASES

The present application is a non-provisional of and claims priority to U.S. provisional application No. 61/791,603, filed on Mar. 15, 2013, which is hereby incorporated by reference in its entirety.

FIELD OF THE INVENTION

The present invention is generally related to methods, devices, and systems related to a sterile drape for a surgical display, such as a drape particularly for use during ophthalmic surgery.

BACKGROUND OF THE INVENTION

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts are fairly common. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humour in the posterior chamber of the eye.

For example, ultrasound from a phacoemulsification system may break up the lens and allow it to be drawn into a treatment probe with an aspiration flow, and a corresponding irrigation flow may be introduced into the eye so that the total volume of fluid in the eye does not change excessively. Conventionally, the phacoemulsification system includes a console and a fluidic cassette mounted on the console. The fluidic cassette is typically changed for each patient and cooperates with the console to provide fluid aspiration.

As such, a phacoemulsification system includes the aforementioned console, which typically provides one or more pumps, such as peristaltic and/or Venturi pumps, for acting on the tubing/fluidics of the cassette in order to provide the referenced irrigation and aspiration. Such a system also generally includes a user interface on the console for controlling and monitoring, among other surgical aspects, the pumps, ultrasound, irrigation and aspiration during surgery. Accordingly, the console generally provides a display, such as an LCD, LED, projection, or similar display, that provides information and status during a surgical procedure. Moreover, the display may serve as the interface mentioned above, at least in so called "touch screen" embodiments. Of course, other interfaces may also be available on the console, such as voice activated control, mechanical knobs and dials, and the like.

It is known that, due to the presence of the aforementioned display in a surgical environment, a sterile cover may be placed at least partially over the display. This cover may eliminate dust, and, in touch screen embodiments, may prevent contamination and/or surgical debris from passing to/from a user onto/from the screen. Such contamination or debris may affect console functionality, and/or may lead to adverse surgical consequences, such as infection.

Such a sterile cover for a phaco console display is disclosed, for example, in U.S. Pat. No. D567,245. However, current sterile drapes for a phaco display are applied as a simple cover, and thus risk breaking the sterile field during application to the phaco display. For example, because of the raised ridge on the display of the console of numerous phaco consoles presently in use, the sterile drape is applied "blindly" and hence subject to the risk of fingers touching the non-sterile top or back of the display ridge. Further, if the sterile field is broken during application of the display drape, the drape must be discarded and replaced, or the risk of contamination is appreciably increased.

Thus, the need exists for a drape for use on a display in a surgical environment that provides improved protection against breakage of the sterile field.

SUMMARY OF THE INVENTION

The present invention is and includes a sterile drape suitable for placement over a display of a phacoemulsification console. The drape includes a first sheet covering a front of the display, a second sheet tied/coupled, at an upper portion thereof, to an upper portion of the first sheet at a first fold at a top of the display, wherein the first fold provides a downward-facing first pocket for fittedly mounting to the top of the display, and a third sheet tied to a lower portion of the second sheet and thereby forming an upward facing second pocket for receiving at least a portion of a user's hand.

The present invention also includes a method of providing a sterile drape for covering a display of a phacoemulsification console. The method may include providing the sterile drape may be provided in a sterile package dedicated for a patient, enabling removal of the sterile drape from the package by a sterile user, providing a finger guard pocket in the sterile drape suitable for receiving fingers of the sterile user, and providing a fitted pocket to allow for fitting of the sterile drape over the display.

Thus, the present invention provides for a drape for use on a display in a surgical environment that provides improved protection against breakage of the sterile field.

BRIEF DESCRIPTION OF THE DRAWINGS

The present invention is best understood with reference to the following detailed description of the invention and the drawings, in which like reference numerals represent like elements, and in which.

DETAILED DESCRIPTION OF THE INVENTION

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical optical and surgical devices, systems, and methods. Those of ordinary skill may recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Figure 1:
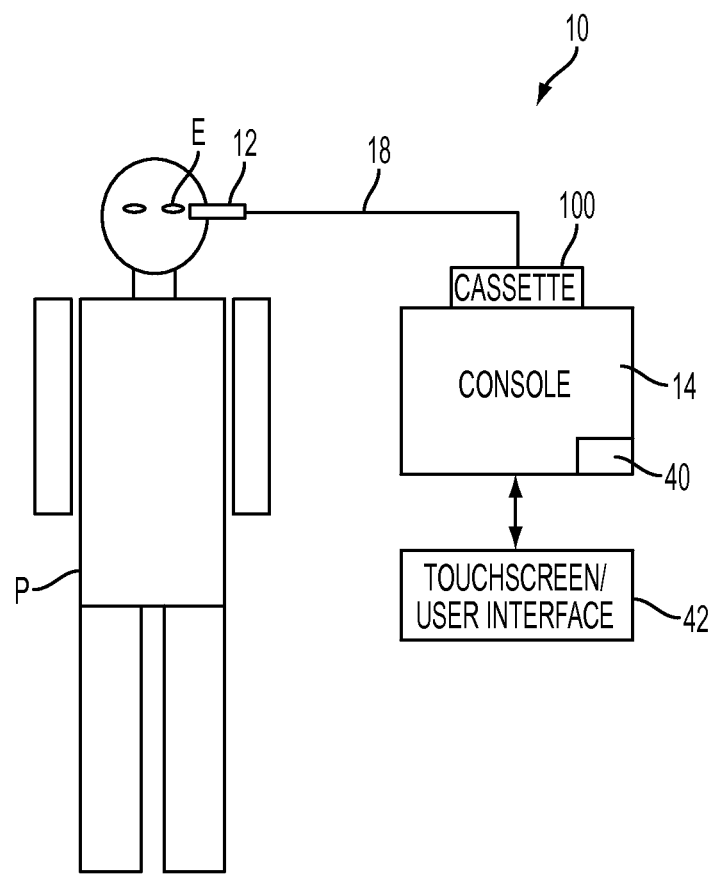
FIG. 1 is a block diagram illustrating a patient and a phacoemulsification console.

Referring to FIG. 1, a phaco system 10 for treating an eye E of a patient P generally includes an eye treatment probe handpiece 12 coupled to a console 14 by a cassette 100 mounted on the console 14. Handpiece 12 may include a handle for manually manipulating and supporting an insertable probe tip. The probe tip has a distal end which is insertable into the eye E, with one or more lumens in the probe tip allowing irrigation fluid to flow from the console 14 and/or cassette 100 into the eye E. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often comprise a disposable (or alternatively, sterilizable) structure, with the surgical fluids being transmitted through flexible conduits 18 of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to a transmitter of the handpiece, a cutter mechanism, or the like. So as to balance the volume of material removed by the aspiration flow, an irrigation flow through handpiece 12 (or a separate probe structure) may also be provided, with both the aspiration and irrigations flows being controlled by console 14.

Controller 40 may include an embedded microcontroller and/or many of the components common to a personal computer, such as a processor, data bus, a memory, input and/or output devices. Such input devices may include a touch screen user interface/display 42. Display 42 will also typically display to a user the status of the aforementioned aspects, and/or other information related to the surgical procedure and/or the surgical environment.

Figure 2:
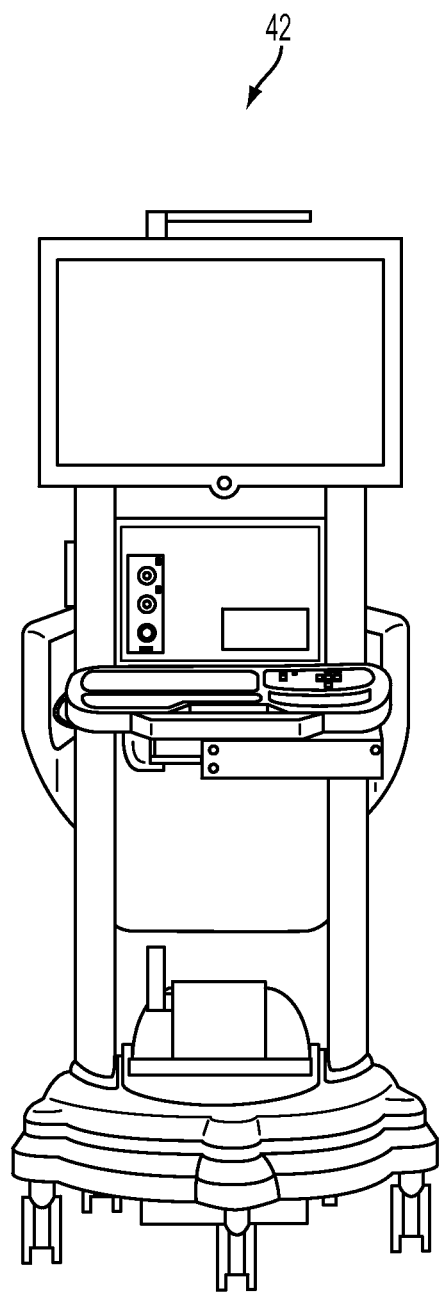
FIG. 2 illustrates a phacoemulsification console.

Many components of console 14 may be found in or modified from known commercial phacoemulsification systems from Abbott Medical Optics Inc. of Santa Ana, Calif.; Alcon Manufacturing, Ltd. of Ft. Worth, Tex.; Bausch and Lomb of Rochester, N.Y.; and other suppliers. An exemplary console, having display/interface 42, is illustrated in FIG. 2.

The user interface/display 42 may thus allow for the controlling and monitoring of surgical aspects during surgery. The display 42 may be a LCD, LED, projection, or similar display, and may provide visual information during the surgical procedure. Moreover, the user interface/display may serve to receive user input that indicates control signals to controller 40, or that requests surgical information to be provided on the display, for example. Because the user interacts with the display/user interface during the surgical procedure, it is highly desirable that a sterile field be maintained with respect to the display 42.

Figure 3A:
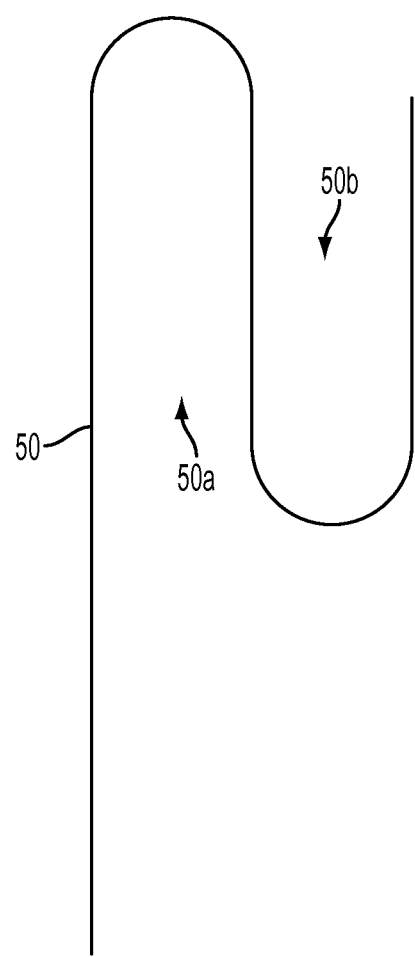
FIGS. 3A, 3B, 3C, and 3D illustrate aspects of a surgical drape according to the disclosure.
Figure 3B:
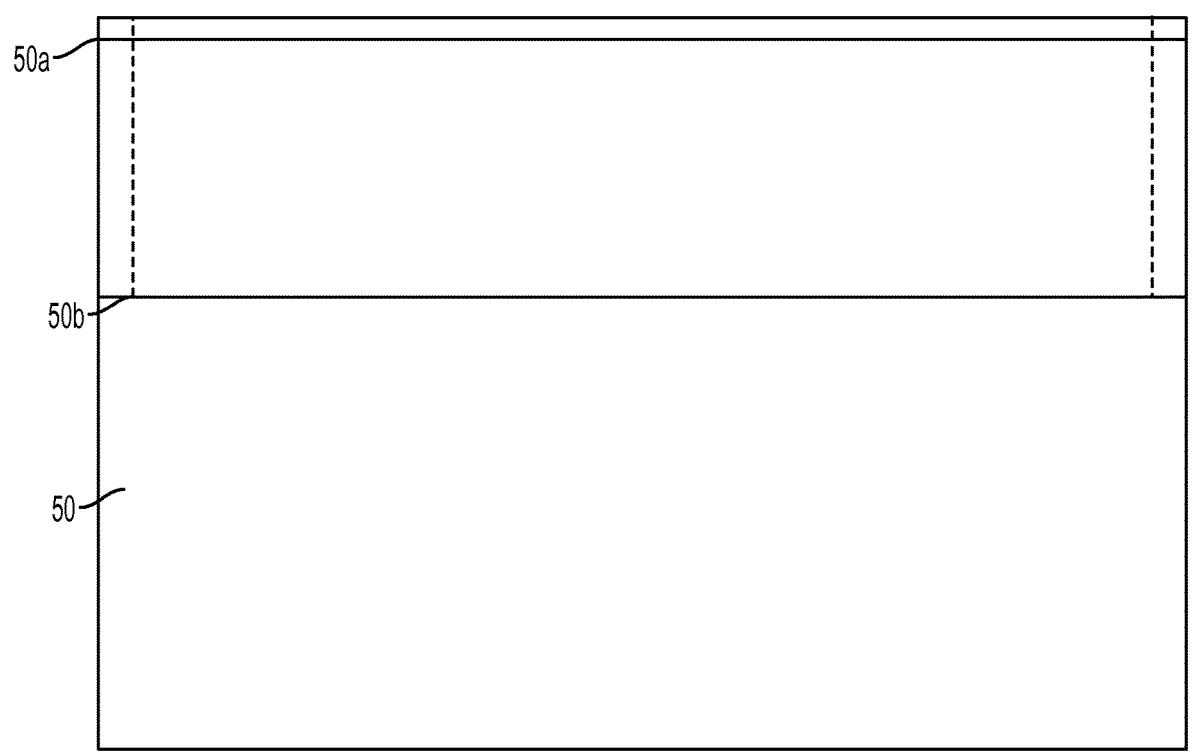
Figure 3C:
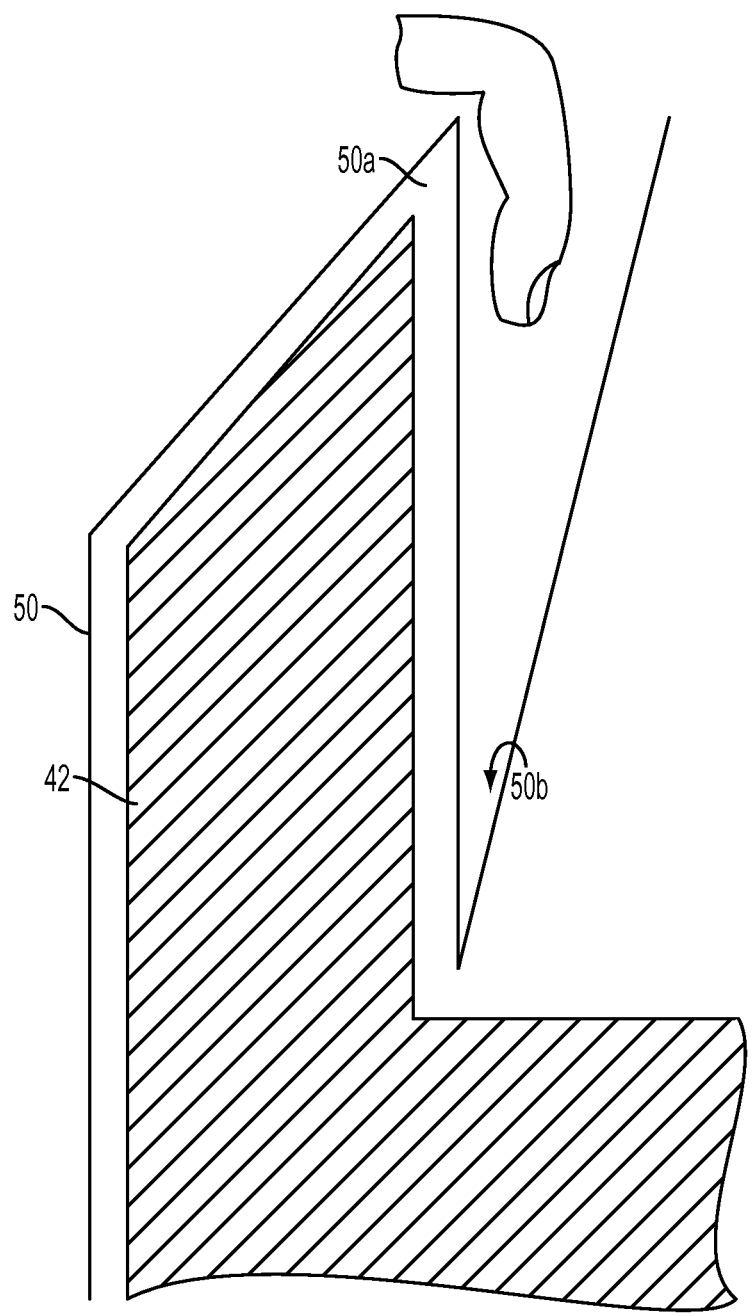
Figure 3D:
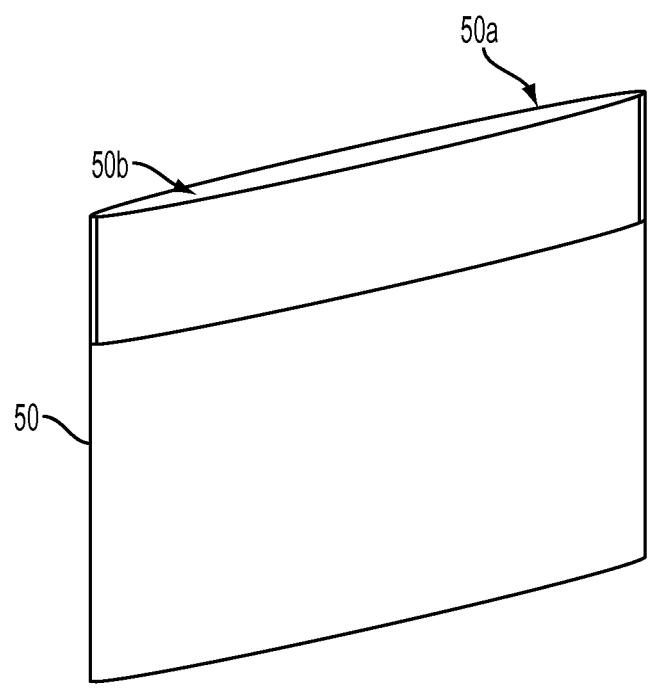

In order to maintain a sterile field, the present invention provides a sterile drape for placement over the display 42 of console 14. The sterile drape 50 is illustrated in FIGS. 3A, 3B, 3C and 3D. The sterile drape 50 comprises a first sheet comprising first opposing surfaces defined between a first top edge and a first bottom edge, a first length defined from the first top edge to the first bottom edge, and a first thickness defined between the first opposing surfaces. The sterile drape 50 further comprises a second sheet comprising second opposing surfaces defined between a second top edge and a second bottom edge, a second length defined from the second top edge to the second bottom edge, and a second thickness defined between the second opposing surfaces. The sterile drape 50 further comprises a third sheet comprising third opposing surfaces defined between a third top edge and a third bottom edge, a third length defined from the third top edge to the third bottom edge, and a third thickness defined between the third opposing surfaces. As can be seen in FIGS. 3C and 3D, the third length and the second length are substantially the same. As shown, the sterile drape 50 includes a fold 50b, at the portion thereof that abuts the rear of display 42 in-situ, which acts as a finger guard during application of drape 50. That is, contrary to known drapes for phaco surgical console displays 42 that comprise a single fold 50a at the top portion thereof in order to allow securing over the top portion of display 42, the instant invention further includes a second fold 50b at the rear of the drape 50. The typical fold 50a has, as shown, the fold opening facing downward with respect to display 42, while the finger guard fold 50b comprises a fold opening facing upward at the rear of display 42. As such, finger guard fold 50b provides an upward facing "pocket" formed by the distal plane (with respect to display 42) of fold 50b and the proximal plane of fold 50b (which is also the rear plane of fold 50a as related to display 42). In embodiments, the larger opening of the drape may cover the display and or the display ridge on the console 42, and the second fold may create a pocket for receiving the fingers or hands of the sterile applicator, e.g. scrub nurse.

Current drapes provide seams on each side of the drape. The present invention, in order to form finger guard fold 50b, may use existing seaming to provide the finger guard, or may add additional seams. Additional seams might include, for example, stitched seams, adhesive-based seams, or the like. Additional seams can increase rigidity for improved handling and durability.

The foregoing embodiment may provide a single, large finger guard fold 50b for receiving a user's hands/fingers. Of course, one or more additional seams may be provided proximate to the center of finger guard fold 50b, such as to provide a pocket for each of the user's hands, individual pockets sized to accommodate fingers for increased control, pockets for a user's hands and additional pockets for placement of items, such as surgical devices, and the like.

The drape 50 may preferably be clear to allow for a user to see and interact with display 42, although aspects of the drape 50 not covering visual display portions of display 50 may be tinted or colored. The drape may be thin, such as to allow for indications by the user to pass readily through the sterile drape to interface 42. For example, each layer of the drape may have a thickness in the range of about 1 to about 3 mils, and, more particularly, may have a thickness of about 1.25 mils. Of course, aspects of the drape 50 that are not covering the visual display portion of display 42, such as folds 50a and 50b, may be of increased thickness, such as to provide increased strength and durability and to thereby avoid tearing. Further, the drape 50 may be formed of any known material suitable for the uses herein and having sufficient strength so as to provide the folds discussed herein, such as blends of low density polyethylene resins.

Figure 4:
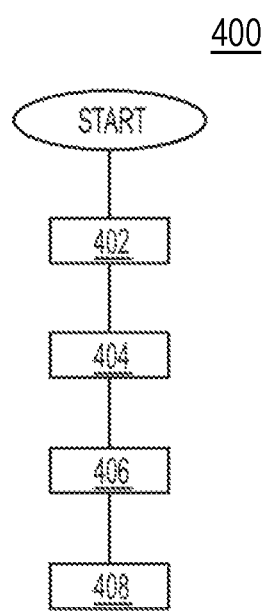
FIG. 4 is a flow diagram illustrating a method according to the disclosure.

FIG. 4 is a flow diagram illustrating a method 400 according to the disclosure. As illustrated, the sterile drape may be provided in a sterile package dedicated for each patient P at step 402. Such a package may also include, for example, the aforementioned cassette for use with a particular patient. The drape may be removed from its packaging by a sterile user, such as a nurse/tech, and may then have folds 50a and 50b opened for use, at step 404. The sterile nurse/tech may then insert his/her fingers into the fold 50b at step 406. The drape 50 may then be placed over the console display at step 408 with no risk to sterile field breach.

It will be appreciated that the disclosed system and method of folding and seaming a sterile drape may be used in environments other than a phacoemulsification surgery. That is, the present invention may be employed anywhere a sterile drape is required or desirable for placement over an object or instrument.

The present invention has provided a sterile display cover, such as a plastic-type sheet that may protect the front surface of a touch screen/display, that may protect the user's palm side hand and the display ridge, and that may protect the sterile user's fingers Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. A sterile drape suitable for placement over a phacoemulsification console display, comprising:
    a first sheet comprising first opposing surfaces defined between a first top edge and a first bottom edge, a first length defined from the first top edge to the first bottom edge, and a first thickness defined between the first opposing surfaces, wherein the first sheet is clear;
    a second sheet comprising second opposing surfaces defined between a second top edge and a second bottom edge, a second length defined from the second top edge to the second bottom edge, and a second thickness defined between the second opposing surfaces;
    the first top edge coupled to the second top edge to define a downward-facing first pocket configured to be fittedly mounted to a top of the phacoemulsification console display, wherein the first length is longer than the second length and the first sheet is configured to drape over an interactive portion of the phacoemulsification console display; and
    a third sheet comprising third opposing surfaces defined between a third top edge and a third bottom edge, a third length defined from the third top edge to the third bottom edge, and a third thickness defined between the third opposing surfaces, the third length and the second length are substantially the same,
    wherein the second bottom edge is coupled to the third bottom edge, thereby defining an upward facing second pocket configured to receive at least a portion of both of a user's hands for positioning the second sheet and the third sheet to cover a back of the phacoemulsification console display with the upward facing second pocket.

2. The sterile drape of claim 1, wherein the first thickness is in a range of 1 to 3 mils.

3. The sterile drape of claim 2, wherein the first thickness is 1.25 mils.

4. The sterile drape of claim 1, wherein the second pocket is sized smaller than the first pocket.

5. The sterile drape of claim 1, wherein the second pocket is divided into multiple pockets by a seam.

6. The sterile drape of claim 1, wherein the second and third sheets are clear.

7. The sterile drape of claim 1, wherein the first, second and third sheets comprise blends of low density polyethylene resins.

8. The sterile drape of claim 1, wherein the first sheet forms an outer most layer of the sterile drape.

9. The sterile drape of claim 1, wherein aspects of the drape not configured to cover the interactive portion of the phacoemulsification console display are tinted or colored.

10. The sterile drape of claim 1, wherein the first top edge and the second top edge are coupled via a fold, wherein the fold has increased thickness relative to the first sheet.

11. A method of providing a sterile drape for covering a phacoemulsification console display, comprising:
    providing the sterile drape in a sterile package, the sterile drape including: a first sheet with a first thickness defined between first opposing surfaces, a second sheet with a second thickness defined between second opposing surfaces, and a third sheet with a third thickness defined between third opposing surfaces;
    enabling removal of the sterile drape from the package by a sterile user;
    providing a downward facing first pocket fitting over the phacoemulsification console display, the first pocket formed by the first sheet being coupled to the second sheet with a first surface area of the first opposing surfaces being greater than a second surface area of the second opposing surfaces such that a first bottom edge of the first sheet extends beyond a second bottom edge of the second sheet; and
    providing an upward facing second pocket formed by the second sheet being coupled to the third sheet, the second pocket configured to receive at least a portion of both of the sterile user's hands for positioning the second sheet and the third sheet to cover a back of the phacoemulsification console display with the second pocket, the second sheet has a first length and the third sheet has a second length substantially the same as the first length.

12. The method of claim 11, wherein the first sheet forms an outer most layer of the sterile drape.

13. The method of claim 11, wherein aspects of the drape not covering an interactive portion of the phacoemulsification console display are tinted or colored.

14. The method of claim 11, wherein wherein the first sheet and the second sheet are coupled via a fold, wherein the fold has increased thickness relative to the first sheet.

15. The method of claim 11, wherein the second pocket is divided into multiple pockets by a seam.

* * * * *